(12) United States Patent
Turcott

(10) Patent No.: US 8,540,643 B1
(45) Date of Patent: Sep. 24, 2013

(54) METHOD AND DEVICE FOR MOTION AND NOISE IMMUNITY IN HEMODYNAMIC MEASUREMENT

(75) Inventor: Robert Turcott, Portola Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 946 days.

(21) Appl. No.: 12/040,091

(22) Filed: Feb. 29, 2008

Related U.S. Application Data

(62) Division of application No. 10/872,165, filed on Jun. 17, 2004, now Pat. No. 7,364,550.

(51) Int. Cl.
*A61B 5/02* (2006.01)
*A61B 5/0295* (2006.01)

(52) U.S. Cl.
USPC ............................................ 600/526; 607/23

(58) Field of Classification Search
USPC ........................................... 600/526; 607/23
See application file for complete search history.

(56) References Cited

U.S. PATENT DOCUMENTS

| | | | |
|---|---|---|---|
| 3,614,954 A | 10/1971 | Mirowski | |
| 3,942,536 A | 3/1976 | Mirowski | |
| 4,686,988 A | 8/1987 | Sholder | |
| 4,708,142 A | 11/1987 | DeCote, Jr. | |
| 4,712,555 A | 12/1987 | Thornander | |
| 4,729,376 A | 3/1988 | DeCote, Jr. | |
| 4,774,950 A | 10/1988 | Cohen | |
| 4,788,980 A | 12/1988 | Mann | |
| 4,809,697 A | 3/1989 | Causey, III | |
| 4,940,052 A | 7/1990 | Mann | |
| 4,944,298 A | 7/1990 | Sholder | |
| 4,944,299 A | 7/1990 | Silvian | |
| 4,967,749 A | 11/1990 | Cohen | |
| 4,969,467 A | 11/1990 | Callaghan | |
| 5,350,410 A | 9/1994 | Kleks | |
| 5,899,927 A | 5/1999 | Ecker | |
| 6,044,298 A | 3/2000 | Salo | |
| 6,058,329 A | 5/2000 | Salo | |
| 6,208,900 B1 | 3/2001 | Ecker | |
| 6,221,024 B1 | 4/2001 | Miesel | |
| 6,249,700 B1 | 6/2001 | Alt | |
| 6,264,611 B1 | 7/2001 | Ishikawa | |
| 6,275,734 B1 | 8/2001 | McClure | |
| 6,409,675 B1 | 6/2002 | Turcott | |
| 6,477,406 B1 | 11/2002 | Turcott | |
| 6,490,486 B1 | 12/2002 | Bradley | |
| 6,491,639 B1 * | 12/2002 | Turcott | 600/508 |

OTHER PUBLICATIONS

Notice of Allowance mailed Jan. 8, 2008: Related U.S. Appl. No. 10/872,165.

(Continued)

*Primary Examiner* — Tammie K Heller
(74) *Attorney, Agent, or Firm* — Steven M. Mitchell

(57) ABSTRACT

A method and device, such as an implantable cardiac device, for motion and noise immunity in hemodynamic measurement is presented. The method includes obtaining a template waveform representing hemodynamic performance of a heart during a first hemodynamic state and obtaining an autocharacterization measure from an autocharacterization (e.g., autocorrelation) of the template waveform. The method further includes obtaining a test waveform during a second hemodynamic state, performing a cross-characterization (e.g., cross-correlation) of the template waveform and test waveform to identify a cross-characterization measure, and comparing the autocharacterization measure with the cross-characterization measure as a measurement of hemodynamic status of the second hemodynamic state. The device includes hardware and/or software for performing the described method.

21 Claims, 7 Drawing Sheets

(56) References Cited

OTHER PUBLICATIONS

Final Office Action mailed Jul. 10, 2007: Related U.S. Appl. No. 10/872,165.

Final Office Action mailed Feb. 28, 2007: Related U.S. Appl. No. 10/872,165.

Non-final Office Action mailed Sep. 11, 2006: Related U.S. Appl. No. 10/872,165.

* cited by examiner

METHOD AND DEVICE FOR MOTION AND NOISE IMMUNITY IN HEMODYNAMIC MEASUREMENT

PRIORITY CLAIM

This application is a Divisional of U.S. patent application Ser. No. 10/872,165, filed Jun. 17, 2004, which is entitled "METHOD AND DEVICE FOR MOTION AND NOISE IMMUNITY IN HEMODYNAMIC MEASUREMENT."

BACKGROUND OF THE INVENTION

1. Field of the Invention

The present invention relates generally to implantable cardiac devices and, more particularly, to implantable cardiac devices capable of hemodynamic measurement.

2. Background Art

An implantable cardiac device is a medical device that is implanted in a patient to monitor electrical activity of the heart and to deliver appropriate electrical and/or drug therapy, as required. Implantable cardiac devices include, for example, pacemakers, cardioverters and defibrillators. The term "implantable cardioverter defibrillator" or simply "ICD" is used herein to refer to any implantable cardiac device capable of delivering therapy to prevent or terminate a fast heart rate or a tachycardia. An ICD employs a battery to power its internal circuitry and to generate electrical therapy. The electrical therapy can include, for example, pacing pulses, cardioverting pulses and/or defibrillator pulses. This is in contrast to a "pacemaker" which is an implantable device specifically intended to treat slow heart rates or bradycardia. However, an ICD provides all the features of a pacemaker. An ICD also includes electrical sensing in its circuitry that monitors the electrical activity of the heart. While performing hemodynamic measurements would be advantageous, at present commercially available ICDs do not perform this function.

Hemodynamic status describes whether the heart is pumping blood sufficiently to ensure adequate perfusion of vital organs. Delivering anti-arrhythmia therapy, via an ICD for example, according to hemodynamic status of an arrhythmia provides several important benefits. Hemodynamically unstable arrhythmias are treated quickly and aggressively, which improves the chance of successful arrhythmia termination. Hemodynamically stable rhythms, during which the patient is most likely to be conscious, are treated with lower voltage therapies. This approach minimizes the risk of painful shocks and conserves battery power of an ICD while at the same time increases the probability of successful arrhythmia termination. Treating a patient according to hemodynamic status measurement may become even more important as the clinical indications for ICD implant become broader.

Hemodynamic status can be measured, for example, by one or more physiologic sensors located within an ICD. One example of a physiologic sensor used for hemodynamic measurement is a hemodynamic sensor. An example of a hemodynamic sensor is an acoustic sensor, which uses an acoustic transducer responsive to heart sounds to detect the hemodynamic status of a patient. For a more detailed description of hemodynamic measurement, including the use of acoustic sensors, see U.S. Pat. No. 6,477,406 B1 (Turcott), which is incorporated herein by reference. Another example of a hemodynamic sensor is a photoplethysmography sensor, such as that described in U.S. Pat. No. 6,409,675 (Turcott), which is incorporated herein by reference. Other types of hemodynamic sensors include intravenous or intracavitory pressure and flow sensors, or optical or mechanical plethysmography sensors. Right ventricular (RV) pressure, for example, is described further in U.S. Pat. Nos. 3,614,954 (Mirowski et al.); 3,942,536 (Mirowski et al.); 4,774,950 (Cohen); 4,967,749 (Cohen); 5,899,927 (Ecker et al.); 6,208,900 (Ecker et al.); 6,221,024 (Miesel); and 6,264,611 (Ishikawa et al.), which are incorporated herein by reference.

Conventional approaches to hemodynamic sensing face a common problem in that it is difficult to provide accurate and reliable data in the face of mechanical artifact. For example, hemodynamic status is particularly difficult to measure due to motion-induced artifact associated with a change of posture and chest compressions that are likely to accompany a significant arrhythmia. Other sources of noise that may affect hemodynamic measurement, depending on the type of hemodynamic sensor used, include electrical noise, external light, changes in atmospheric pressure, and radiated energy.

What is needed is a device, such as an ICD, that is immune from motion and noise during hemodynamic measurement and can reliably use such hemodynamic measurement to deliver an appropriate electrical therapy.

BRIEF SUMMARY OF THE INVENTION

The following invention is a method and device that minimize the deleterious effect of noise on hemodynamic sensing algorithms. The present invention is effective for any kind of noise. The source of the noise can include, for example, mechanical artifact associated with motion or change in posture, electrical noise such as thermal and flicker noise, environmental nose such as changes in atmospheric pressure or radiant energy, or any other process or cause that corrupts the measured signal. Conventional ICDs and related signal processing techniques do not resolve this problem. It is important to note that applications of the invention are not limited to hemodynamic assessment, but may be applied to the assessment of any signal. When used during hemodynamic assessment, however, applications of the technique are not limited to hemodynamic assessment during arrhythmia detection. Rather, the technique can be used in any context that requires hemodynamic measurement, such as atrio-ventricular/ventricular-ventricular (AV/VV) optimization, disease monitoring, orthostatic hypotension detection, and therapy, for example.

A method and device, such as an implantable cardiac device, for motion and noise immunity in hemodynamic measurement is presented. According to embodiments of the invention, the method includes obtaining a template waveform representing hemodynamic performance of a heart during a first hemodynamic state and obtaining an autocharacterization measure from an autocharacterization (e.g., autocorrelation) of the template waveform. The method further includes obtaining a test waveform during a second hemodynamic state, performing a cross-characterization (e.g., cross-correlation) of the template waveform and test waveform to identify a cross-characterization measure, and comparing the autocharacterization measure with the cross-characterization measure as a measurement of hemodynamic status of the second hemodynamic state. According to embodiments of the invention, the device includes hardware and/or software for performing the described method. A method and device for selecting an appropriate anti-arrhythmia therapy for a patient according to the patient's hemodynamic status are also disclosed.

Further features and advantages of the invention as well as the structure and operation of various embodiments of the invention are described in detail below with reference to the accompanying drawings.

BRIEF DESCRIPTION OF THE DRAWINGS/FIGURES

The accompanying drawings, which are incorporated herein and form part of the specification, illustrate the invention and, together with the description, further serve to explain the principles of the invention and to enable a person skilled in the relevant art(s) to make and use the invention. In the drawings, like reference numbers indicate identical or functionally similar elements. Additionally, in most drawings, the leftmost digit of a reference number identifies the drawing in which the reference number first appears.

DETAILED DESCRIPTION OF THE INVENTION

The following detailed description of the invention refers to the accompanying drawings that illustrate exemplary embodiments consistent with this invention. Other embodiments are possible, and modifications may be made to the embodiments within the spirit and scope of the invention. Therefore, the following detailed description is not meant to limit the invention. Rather, the scope of the invention is defined by the appended claims.

It will be apparent to one of skill in the art that the invention, as described below, may be implemented in many different embodiments of hardware, software, firmware, and/or the entities illustrated in the figures. Any actual software and/or hardware described herein is not meant to limit the scope of the invention. Thus, the structure, operation and behavior of the invention will be described with the understanding that many modifications and variations of the embodiments are possible, given the level of detail presented herein.

Figure 1A:
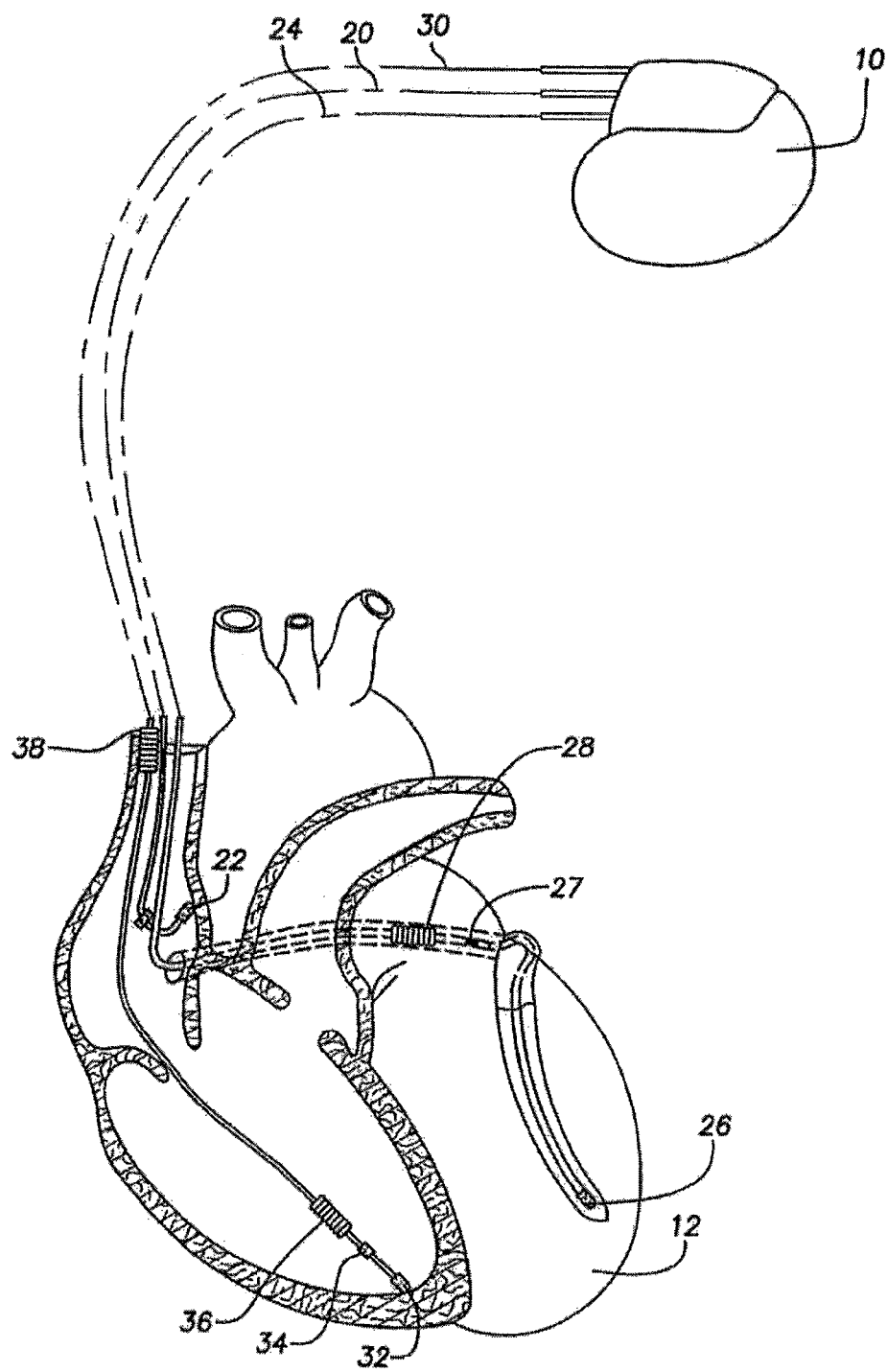
FIG. 1A is a simplified diagram illustrating an exemplary ICD in electrical communication with at least three leads implanted into a patient's heart for delivering multi-chamber stimulation and shock therapy.
Figure 1B:
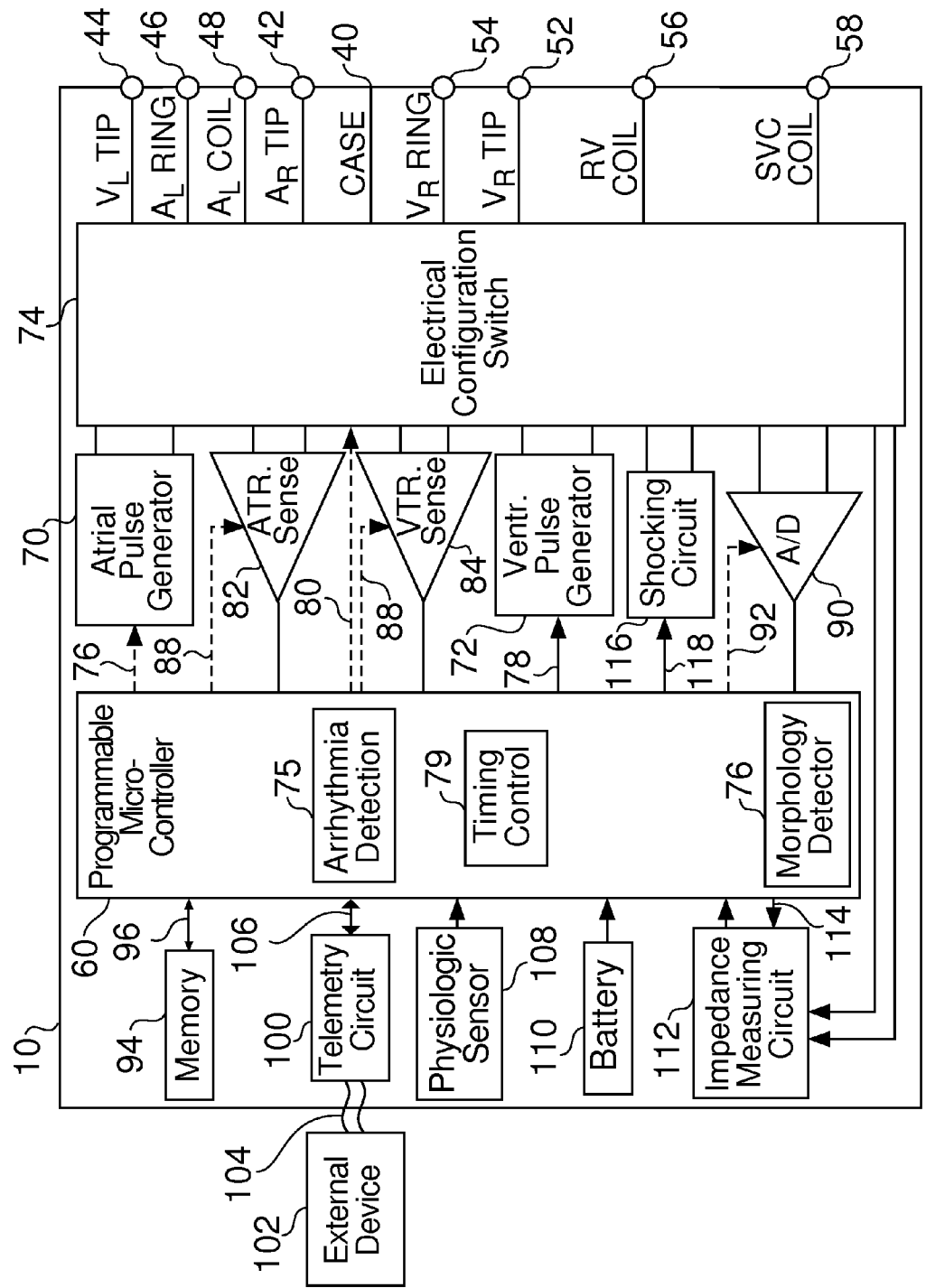
FIG. 1B is a functional block diagram of an exemplary ICD, which can provide cardioversion, defibrillation and pacing stimulation in four chambers of a heart.

Before describing the invention in detail, it is helpful to describe an example environment in which the invention may be implemented. The invention is particularly useful in the environment of an implantable cardiac device. Implantable cardiac devices include, for example, pacemakers, cardioverters and defibrillators. The term "implantable cardioverter defibrillator" or simply "ICD" is used herein to refer to any implantable cardioverter defibrillator ("ICD") or implantable cardiac device capable of delivering therapy. FIGS. 1A and 1B illustrate such an environment.

As shown in FIG. 1A, there is an exemplary ICD 10 in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the superior vena cava. Accordingly, right ventricular lead 30 is capable of receiving cardiac signals and delivering stimulation in the form of pacing and shock therapy to the right ventricle.

FIG. 1B shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 1B, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

At the core of ICD 10 is a programmable microcontroller 60 which controls the various modes of stimulation therapy. As is well known in the art, microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the invention. Rather, any suitable microcontroller 60 can be used to carry out the functions described herein. The use of microprocessor-based control circuits for performing timing and data analysis functions are well known in the art. In specific embodiments of the invention, microcontroller 60 performs some or all of the steps associated with the sensing and prevention therapy in accordance with the invention.

Representative types of control circuitry that may be used with the invention include the microprocessor-based control system of U.S. Pat. No. 4,940,052 (Mann et al.) and the state-machines of U.S. Pat. Nos. 4,712,555 (Thornander et al.) and 4,944,298 (Sholder). For a more detailed description of the various timing intervals used within the ICDs and their inter-relationship, see U.S. Pat. No. 4,788,980 (Mann et al.). The '052, '555, '298 and '980 patents are incorporated herein by reference.

As shown in FIG. 1B, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses.

Microcontroller 60 further includes timing control circuitry 79 which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic sensitivity control, bandpass filtering, and a threshold detection circuit, as known in the art, to selectively sense the cardiac signal of interest. The automatic sensitivity control (ASC) enables ICD 10 to deal effectively with the difficult problem of sensing the low amplitude signal characteristics of atrial or ventricular fibrillation. Such sensing circuits, 82 and 84, can be used to determine cardiac performance values used in the invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 84.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detection circuitry 75 and morphology detection circuitry 76 to recognize and classify arrhythmia so that appropriate therapy can be delivered.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Advantageously, data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (DeCote, Jr.); U.S. Pat. No. 4,708,142 (DeCote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference. The type of capture detection system used is not critical to the invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of ICD 10 may be non-invasively programmed into memory 94 through a telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through an established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

In an embodiment, ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.) in accordance with the embodiments of the invention. Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

ICD 10 additionally includes a battery 110, which provides operating power to all of the circuits shown in FIG. 1B. For ICD 10, which employs shocking therapy, battery 110 must be capable of operating at low current drains for long periods of time, and then be capable of providing high-current pulses (for capacitor charging) when the patient requires a shock pulse. Battery 110 must also have a predictable discharge characteristic so that elective replacement time can be detected. Accordingly, ICD 10 preferably employs lithium/silver vanadium oxide batteries, as is true for most (if not all) current devices.

ICD 10 further includes magnet detection circuitry (not shown), coupled to microcontroller 60. It is the purpose of the magnet detection circuitry to detect when a magnet is placed over ICD 10, which magnet may be used by a clinician to perform various test functions of ICD 10 and/or to signal microcontroller 60 that the external programmer 102 is in place to receive or transmit data to microcontroller 60 through telemetry circuit 100.

As further shown in FIG. 1B, ICD 10 is shown as having an impedance measuring circuit 112 which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 116 by way of a control signal 118. The shocking circuit 116 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognized), and pertaining exclusively to the treatment of fibrillation. Accordingly, microcontroller 60 is capable of controlling the synchronous or asynchronous delivery of the shocking pulses.

With the description of an example environment, such as an ICD, in mind, features of the invention are described in more detail below.

As stated in the Background section, hemodynamic status describes whether the heart is pumping blood sufficiently to ensure adequate perfusion of vital organs. Hemodynamic status can be measured, for example, by one or more physiologic sensors located within an ICD, or on a lead that is placed in the bloodstream or at a location remote from the ICD. One example of a physiologic sensor used for hemodynamic measurement is a hemodynamic acoustic sensor. An acoustic sensor uses an acoustic transducer responsive to heart sounds to detect the hemodynamic status of a patient. For a more detailed description of hemodynamic measurement, including the use of acoustic sensors, see U.S. Pat. No. 6,477,406 B1 (Turcott), which is incorporated herein by reference. Another example of a hemodynamic sensor is a photoplethysmography sensor, such as that described in U.S. Pat. No. 6,409,675 (Turcott), which is incorporated herein by reference. Yet another example of a hemodynamic sensor is a pressure transducer placed in the right ventricle, as described in U.S. Pat. Nos. 3,942,536 (Mirowski et al.) and 6,221,024 (Miesel), which are incorporated herein by reference.

Conventional approaches to hemodynamic sensing face the common problem that it is difficult to provide accurate and reliable data in the face of mechanical artifact. For example, hemodynamic status is particularly difficult to measure due to motion-induced artifact associated with a change of posture and chest compressions that are likely to accompany a significant arrhythmia. To counter this problem, a device is needed, such as an ICD, that is immune from motion and electrical noise during hemodynamic measurement and can reliably use such hemodynamic measurement to deliver an appropriate electrical therapy. To that end, a device and method for hemodynamic measurement that is immune from motion and electrical noise, according to embodiments of the invention, will now be described.

Figure 2:
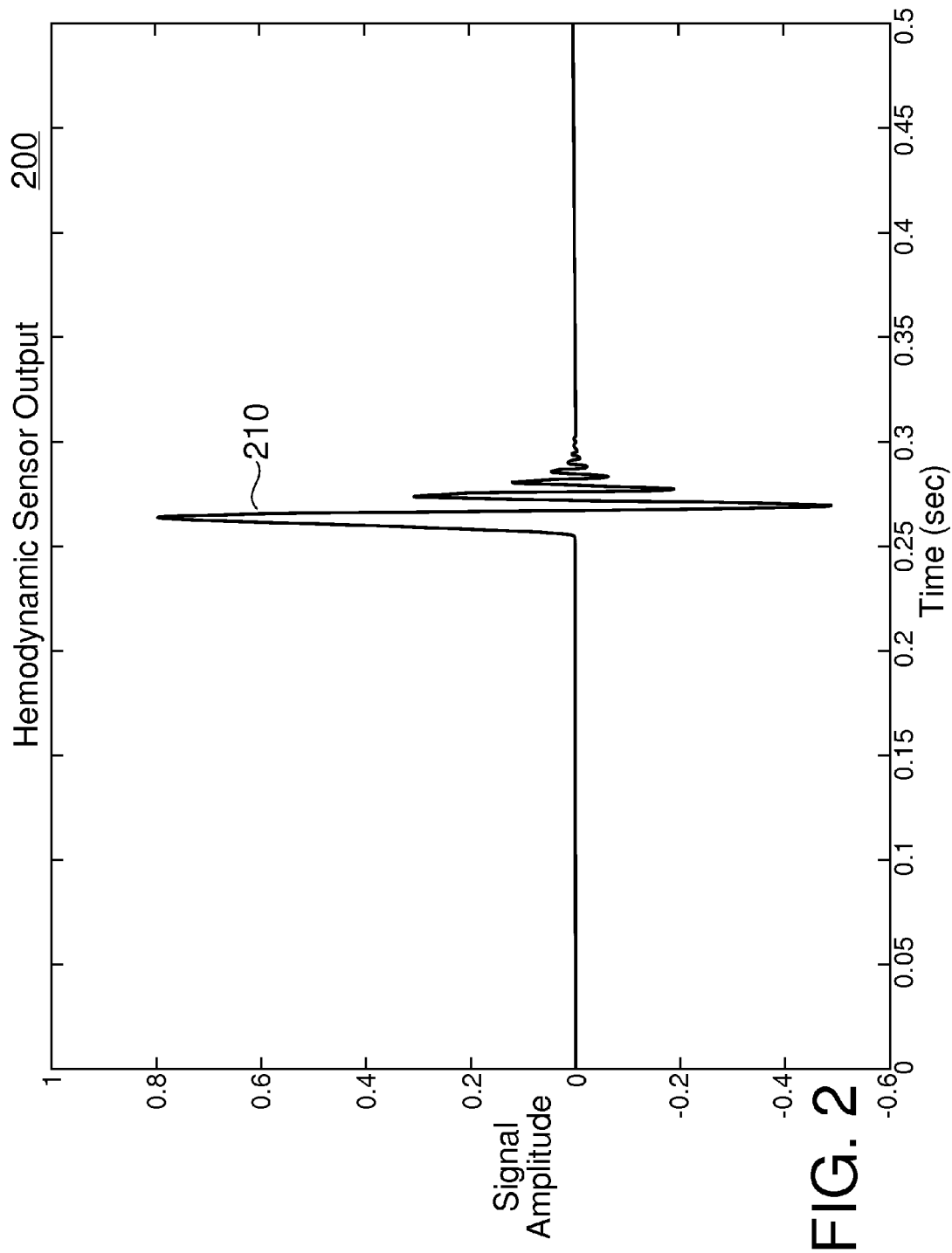
FIG. 2 illustrates a graphical output of a hemodynamic sensor, as signal amplitude versus time, that represents an exemplary template waveform for a hemodynamic sensor as used in embodiments of the invention.

FIG. 2 shows a graph 200 of an exemplary output from a hemodynamic sensor, such as an acoustic or photoplethysmography sensor. The signal of graph 200 is, for example, a template waveform 210 measured during a first hemodynamic state, plotted as signal amplitude versus time. Template waveform 210 should represent hemodynamic sensor data during a known physiologic state, such as during a benign state such as sinus rhythm. Therefore, the first hemodynamic state may be a normal sinus rhythm or pacing with a baseline AV delay, for example.

The template waveform 210 shown in FIG. 2 is a model of an ideal sensor output unaffected by noise. However, most hemodynamic signals contain noise and artifact that can degrade the quality of a template. Examples of such noise include electronic noise and respiration. Electronic noise is recognizable as low amplitude, high frequency variability of the signal, which gives the trace a thick appearance in the plot. Respiration is recognizable as a low-frequency oscillation in the baseline of the hemodynamic signal. To minimize the effects of electronic, respiratory, and other noise components, the raw hemodynamic signal can be filtered using a band-pass filter, for example. Some intrinsic respiratory variability may remain, but it is greatly attenuated relative to the raw signal.

To acquire a template waveform that best represents a non-pathologic rhythm, the template waveform can be formed by superimposing multiple pulse traces in time and computing an ensemble average over one or more respiratory cycles. This can be done by synchronizing the traces relative to sensed cardiac events. For example, a threshold crossing of an ECG is used to identify a point of onset of ventricular contraction. The portions of the filtered hemodynamic signal that fall between successive threshold crossings are superimposed, and the average of the ensemble of traces is computed. The result serves as the template waveform. Other methods of obtaining a template exist and are known in the art. For example, rather than performing the alignment based on synchronization with an auxiliary signal, as discussed above in reference to the ECG signal, one could align the traces by performing a cross-correlation between a trace and the current template or a reference trace.

The quality of the template can be further improved by acquiring the template data during periods when noise is not present or is minimally present. For example, by monitoring an activity sensor, which is commonly included in contemporary ICDs, template data could be acquired when the patient is not moving. Alternatively, intrinsic analysis of the hemodynamic sensor signal could be performed to select periods when the signal fidelity is high, which implies that motion and other sources of noise are not significant. High-fidelity data segments could then be used to construct the template.

Figure 3:
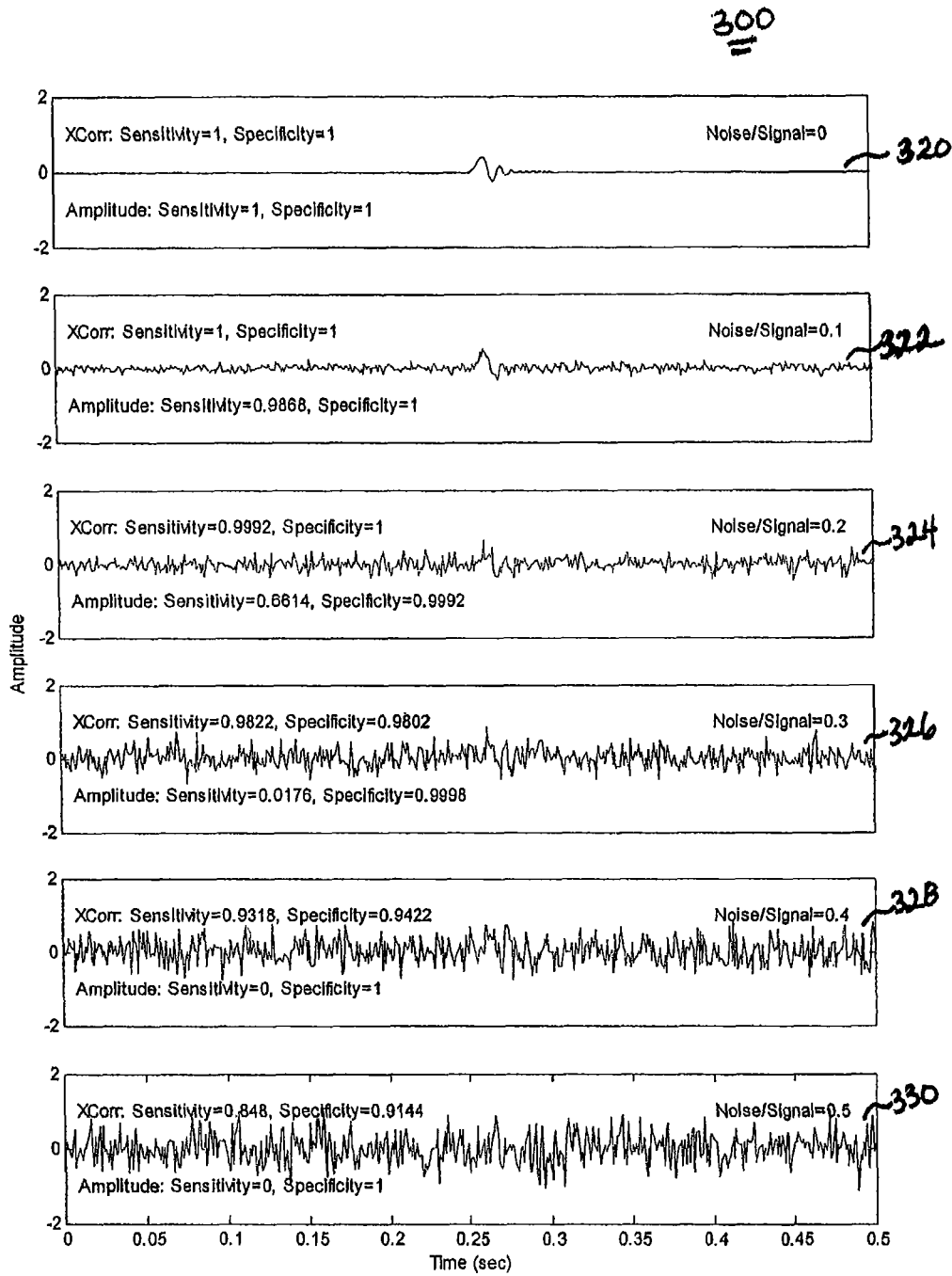
FIG. 3 illustrates a series of sample test waveforms with varying levels of white Gaussian noise, as used in embodiments of the invention.
Figure 4:
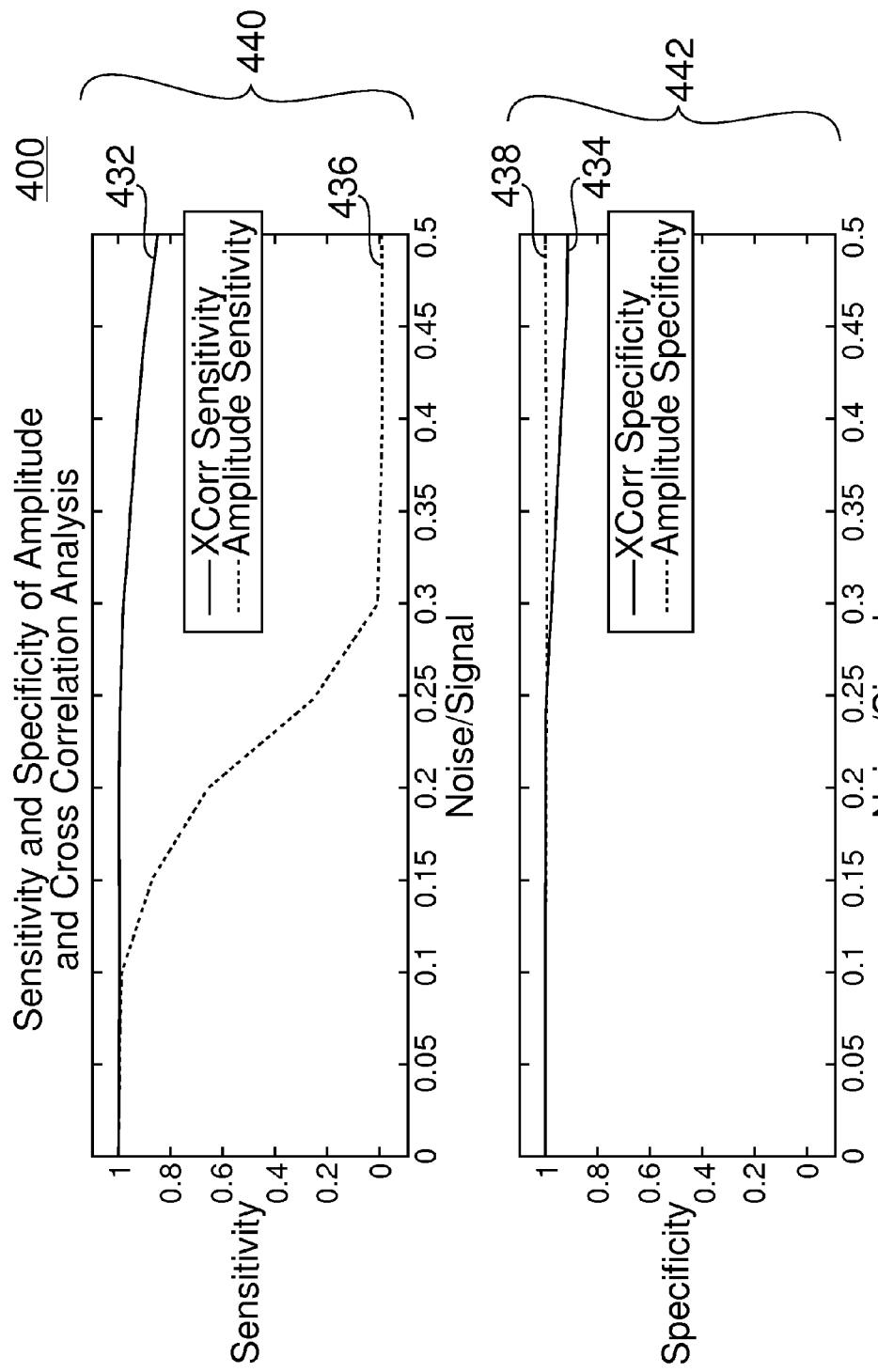
FIG. 4 illustrates a graphical representation of the sensitivity and specificity of both a conventional amplitude analysis and the cross-correlation analysis of the invention, plotted as functions of noise level.

FIG. 3 illustrates an examplary series 300 of test waveforms 320-330 with varying levels of white Gaussian noise applied. In FIG. 3, the standard deviation of the additive noise is varied from 0.0 (as shown by test waveform 320) to 0.5 (as shown by test waveform 330) times the maximum of the full-amplitude noiseless test waveform 320. As the noise amplitude is increased, note how quickly the waveform of interest becomes obscured. The invention allows the measuring of hemodynamic performance that is essentially unaffected by increases in noise amplitude. FIG. 4 corresponds to the test waveforms 320-330 of FIG. 3 and will be discussed after the embodiments of the invention are described.

In the description to follow, the terms 'autocorrelation' and 'cross-correlation' are used. These terms refer to well-known mathematical operations that are commonly used in engineering and data analysis. Their use in the following description is illustrative, and should not be taken in a limiting sense. The terms 'autocorrelation' and 'cross-correlation' represent specific techniques of a more general class of mathematical operations, which are referred to herein as 'autocharacterization' and 'cross-characterization.' Any technique that provides a quantitative comparison of two waveforms can serve in place of the autocorrelation and cross-correlation steps described below.

An example technique of quantitative comparison of two waveforms is as follows. Point-wise differences between two waveforms can be calculated, squared, and summed. One waveform is then translocated relative to the other, and the calculation repeated. This process is continued so that a function is obtained which expresses the dependence of the sum of squared differences between the two waveforms on the relative translocation of the two waveforms. This is similar to the correlation function, except that here it is the sum of squared differences, while the correlation function is based on average squared value. The minimum value achieved by this function occurs at the time lag or translocation that yields the best fit between the two waveforms, whereas the maximum value of a correlation function occurs at the time lag or translocation that yields the worst fit.

Alternatively, rather than obtaining a function whose independent variable is the time lag, or translocation, between the two waveforms, one could calculate a single measure of similarity at a single lag or translocation. For example, aligning two functions relative to ventricular depolarization (e.g., as measured by an intracardiac electrogram) and obtaining a measure that represents their degree of similarity would avoid the need for repetitive translocations and calculations described above and implicit in the computation of the correlation function. The degree of similarity could be quantified as the sum of squared differences, or, analogous to the correlation function, the sum of squared values. Thus, while the invention is described in terms of the autocorrelation and cross-correlation operations, these terms are intended to represent a broader class of operations, which are more appropriately termed 'autocharacterization' and 'cross-characterization.'

Embodiments of the invention will now be described.

Figure 5:
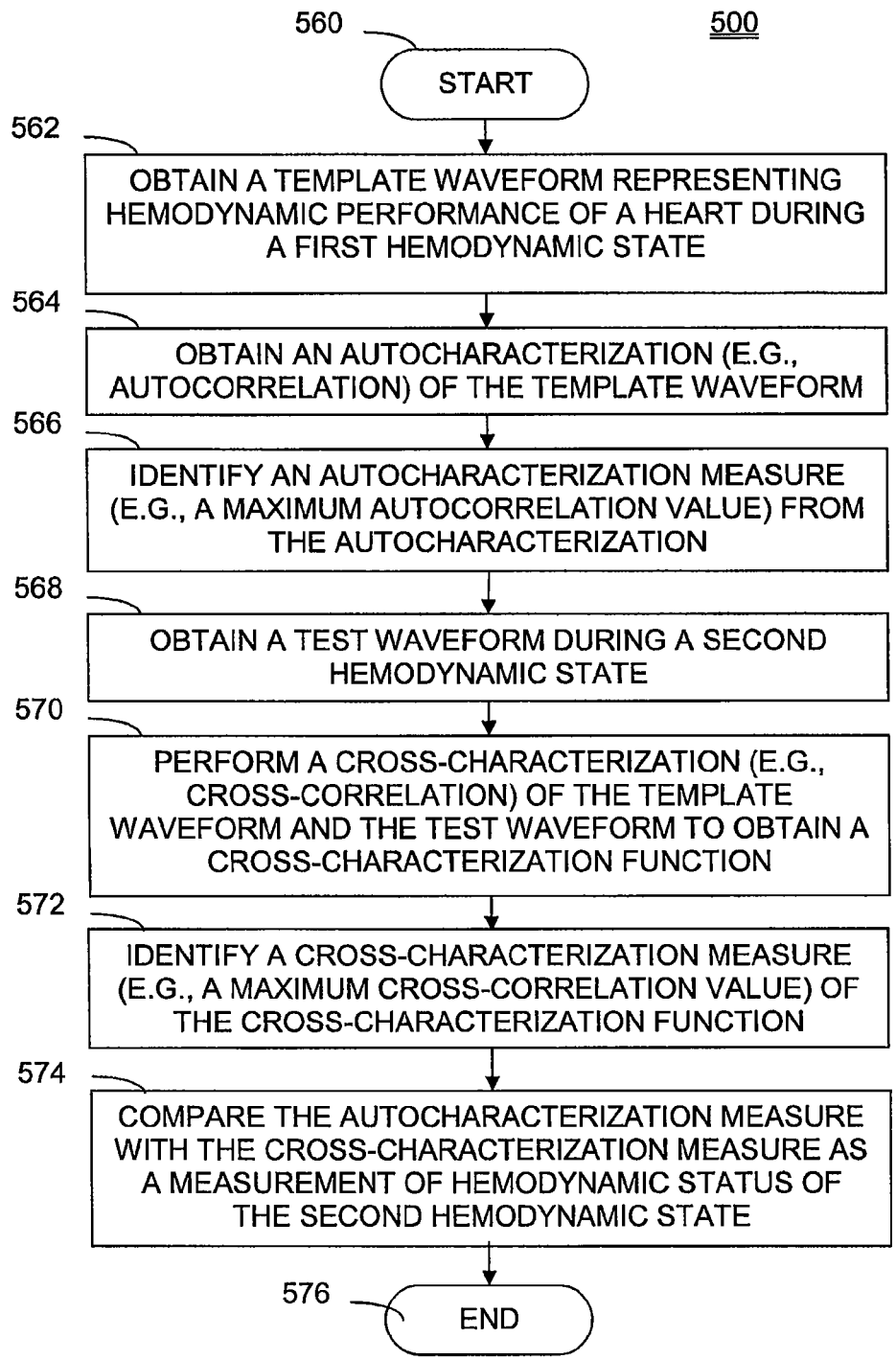
FIG. 5 is a flowchart illustrating an embodiment of a method of the invention in which a hemodynamic performance of a patient's heart is measured.

A method 500 of measuring hemodynamic performance of a patient's heart in accordance with the invention is illustrated in the flowchart of FIG. 5. According to an embodiment of the invention, the method 500 begins at step 560, and immediately continues at step 562. In step 562, a template waveform is obtained that represents hemodynamic performance of a heart during a first hemodynamic state. The template waveform is akin to template waveform 210 of FIG. 2, which represents output from a physiologic sensor such as an acoustic or photoplethysmography sensor. According to one embodiment of the invention, the first hemodynamic state is that of a normal sinus rhythm. According to another embodiment of the invention, the first hemodynamic state is heart pacing with a baseline atrioventricular (AV) delay.

In step 564, an autocorrelation of the template waveform is obtained. The autocorrelation may be obtained in any way that is known by those skilled in the art of signal processing. One example of performing an autocorrelation of the template waveform is to transform the template waveform signal into the frequency domain from the time domain, multiply its spectrum with itself, and perform an inverse transformation back into the time domain. In step 566, a maximum autocorrelation value is identified from the obtained autocorrelation.

In step 568, a test waveform is obtained during a second hemodynamic state. The test waveform is akin to any of test waveforms 320-330 of FIG. 3. The test waveform represents current output from a physiologic sensor such as an acoustic or photoplethysmography sensor. According to one embodiment of the invention, the second hemodynamic state is that of a tachycardia rhythm. According to another embodiment of the invention, the second hemodynamic state includes a test atrioventricular (AV) delay. That is, the AV delay can be varied and the resultant test waveforms captured for the different AV delay values.

In step 570, a cross-correlation of the template waveform and the test waveform is performed to obtain a cross-correlation function. The cross-correlation may be obtained in any way that is known by those skilled in the art of signal processing. One example of performing a cross-correlation of the template waveform with the test waveform is to transform both waveform signals into the frequency domain from the time domain, multiply the spectrum of the template waveform with the spectrum of the test waveform, and perform an inverse transformation back into the time domain. In step 572, a maximum value of the cross-correlation function is obtained.

In step 574, the maximum autocorrelation value is compared with the maximum cross-correlation function value. This comparison is a measurement of hemodynamic status of the second hemodynamic state with the template waveform being used as a baseline. In an embodiment of the invention, step 574 includes comparing a predetermined threshold against a difference between the maximum autocorrelation value and the maximum cross-correlation function value. Method 500 terminates at step 576.

According to one embodiment of the invention, step 574 includes determining if the maximum cross-correlation function value is less than the maximum autocorrelation value by a predetermined status low threshold. If so, the hemodynamic status of the second hemodynamic state is determined as low. This means that the current hemodynamic status of the patient is deemed to be significantly less than during template waveform acquisition. This may mean, for example, that the detected tachycardia is hemodynamically unstable or that the current test AV delay is inferior to the baseline AV delay. The magnitude of the threshold can vary according to the application. For example, a different threshold may be used for arrhythmia analysis than would be used for AV/VV optimization.

According to another embodiment of the invention, step 574 includes determining if the maximum cross-correlation function value is greater than the maximum autocorrelation value by a predetermined status high threshold. If so, the hemodynamic status of the second hemodynamic state is determined as high. This means that the current hemodynamic status of the patient is deemed to be significantly greater than during template waveform acquisition. This may mean, for example, that the current test AV delay is superior to the baseline AV delay. The magnitude of the threshold can vary according to the application.

The maximum cross-correlation function value is reduced by a reduction in signal amplitude and also by a deviation of signal morphology away from that of the template. The reduction in signal amplitude and deviation of signal morphology are expected for some hemodynamic sensors during unstable arrhythmias. Both effects (amplitude and morphology) on the maximum values are in the same direction and improve performance during arrhythmia discrimination.

Figure 6:
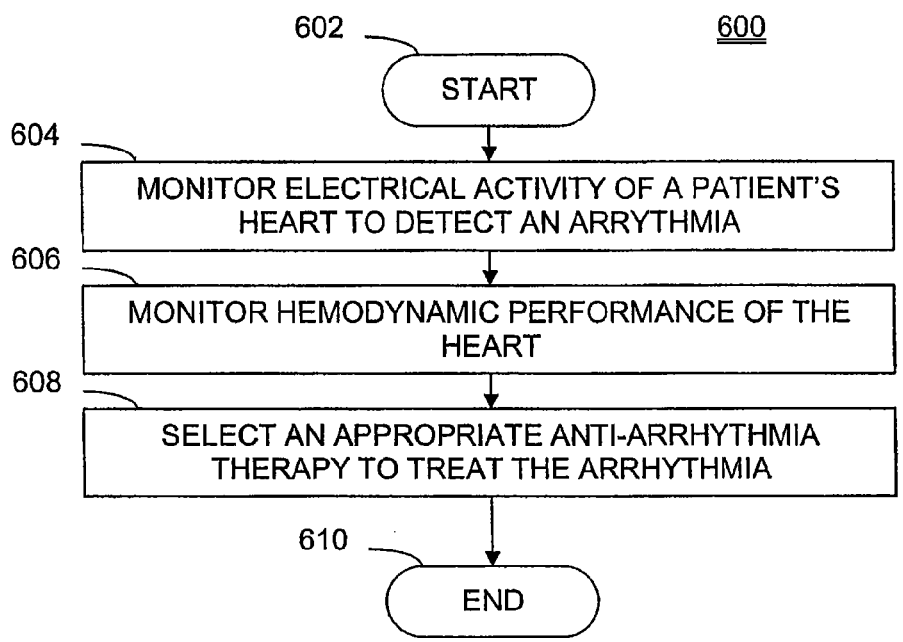
FIG. 6 is a flowchart illustrating another embodiment of a method of the invention in which an appropriate anti-arrhythmia therapy according to a hemodynamic status of a patient is selected.

A method 600 of selecting an appropriate anti-arrhythmia therapy for a patient according to the patient's hemodynamic status, in accordance with the invention, is illustrated in the flowchart of FIG. 6. According to an embodiment of the invention, the method 600 begins at step 602, and immediately continues at step 604. In step 604, electrical activity of a patient's heart is monitored to detect an arrhythmia. In step 606, hemodynamic performance of the heart is monitored. In an embodiment, hemodynamic performance is monitored as in method 500, previously described with reference to FIG. 5. In step 608, an appropriate anti-arrhythmia therapy is selected to treat the arrhythmia. One factor involved with this selection is whether the patient is hemodynamically stable or unstable. For example, if hemodynamically stable, the patient is likely to be conscious, and therefore treated with lower voltage therapies. If hemodynamically unstable, the patient is treated more quickly and aggressively. In step 610, the method terminates.

As stated earlier, it is important to note that applications of the invention are not limited to hemodynamic assessment, but may be applied to the assessment of any electrical signal. When used during hemodynamic assessment, however, applications of the technique are not limited to hemodynamic assessment during arrhythmia detection. Rather, the technique can be used in any context that requires hemodynamic measurement, such as atrio-ventricular/ventricular-ventricular (AV/VV) optimization, disease monitoring, orthostatic hypotension detection and therapy, for example.

It will be appreciated by those skilled in the art that the above-described method can be used within the hardware, software, and/or firmware of a pacing system, such as the ICD described earlier with reference to FIGS. 1A and 1B, for example.

The technique of method 500 functions reliably in the face of electrical noise and motion artifact since the maximum cross-correlation function value is relatively unaffected by additive noise. This is demonstrated further with reference to FIGS. 2, 3, and 4, which show a computer-simulated comparison between a conventional amplitude-based technique as compared to the cross-characterization technique of the invention.

As previously described, the waveform 210 of FIG. 2 serves as a template waveform showing output from a physiologic sensor, such as an acoustic or photoplethysmography sensor. Template waveform 210 is cross-correlated with a test waveform, such as any of test waveforms 320-330 of FIG. 3. The test waveforms 320-330 represent current output of the physiologic sensor, each with varying levels of white Gaussian noise applied. Test waveform 320 has no noise applied, for example, and test waveform 324 has a standard deviation of additive noise of 0.2 times the maximum of the full-amplitude test waveform with no noise applied (i.e., test waveform 320). The template waveform 210 is cross-correlated with each of test waveforms 320-330, and the maximum of each of the resulting functions is taken as a measure of hemodynamic status.

In the computer simulation of which this discussion describes a part, ten thousand test waveforms were analyzed at each of a range of noise levels. Half of the test waveforms had the same amplitude as the original template waveform, while the remainder had a 50% attenuation in amplitude. The sensitivity and specificity of the cross-correlation technique of the invention in detecting the reduced amplitude signal was determined. The sensitivity and specificity of the cross-correlation technique was then compared to the sensitivity and specificity of a conventional amplitude-based technique used to analyze the same set of test waveforms. The algorithm used for the computer simulation was tasked with detecting a 50% reduction in signal amplitude. The detection threshold for the cross-correlation technique was halfway between a maxima of the cross-correlation functions (i.e., template waveform crossed with a full-amplitude noiseless test waveform, and template waveform crossed with a half-amplitude noiseless test waveform). The detection threshold for the amplitude technique was halfway between a maxima of a full-amplitude noiseless test waveform and a half-amplitude noiseless test waveform.

In FIG. 3, the sensitivity and specificity for the conventional amplitude technique and the cross-correlation technique of the invention are shown for each test waveform 320-330. It can be seen that for low noise levels, both techniques can reliably distinguish the full-amplitude from the half-amplitude test waveforms, since each technique shows a sensitivity and specificity of at or very near 100% (see the sensitivities and specificities of test waveforms 320 and 322). However, for higher noise levels, the amplitude technique fails. For example, the sensitivities of the amplitude technique for test waveforms 326, 328, and 330 are at or very nearly zero, while the specificities are at or nearly one. This indicates that for test waveforms 326, 328, and 330, the amplitude technique diagnosed all test waveforms as being of full amplitude. It is unlikely that a threshold adjustment would show improvement.

FIG. 4 corresponds to the test waveforms 320-330 of FIG. 3 and illustrates a comparison of the sensitivities and specificities of a conventional amplitude technique and the cross-correlation technique of the invention for detecting a 50% reduction in signal amplitude. The calculated sensitivities and specificities shown in FIG. 3 are plotted as functions 400 of noise level. Solid lines 432 and 434 represent the data from using the cross-correlation technique of the invention. The dashed lines 436 and 438 represent the data from using the conventional amplitude-based technique. The sensitivity chart 440 clearly shows the difference in sensitivity between the two techniques at normalized noise levels greater than about 0.2. The results of the simulation show that even though the presence of the test waveforms becomes difficult to visually detect in the raw data for normalized noise levels greater than about 0.2 (see FIG. 3), the sensitivity and specificity of the cross-correlation technique remains quite good for all noise levels tested (as shown in FIG. 4).

The cross-characterization technique of the invention described herein significantly improves noise-immunity in hemodynamic sensing as compared to conventional techniques. Use of cross-characterization techniques, such as cross-correlation, allows for hemodynamic measurement that is immune from motion and noise and can reliably be used to deliver appropriate electrical therapies to a patient, possibly even enabling ambulatory hemodynamic assessment.

Example embodiments of the methods, systems, and components of the invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the invention should not be limited by any of the above-described exemplary embodiments, but should be defined only in accordance with the following claims and their equivalents.

What is claimed is:

1. A method of selecting an appropriate anti-arrhythmia therapy for a patient according to a hemodynamic status of the patient, comprising:
    monitoring electrical activity of the patient's heart to detect an arrhythmia;
    monitoring hemodynamic performance of the heart, said monitoring comprising:
        measuring a parameter indicative of hemodynamic performance during a first state to establish a template waveform,
        obtaining an autocharacterization measure for the template waveform by cross-characterizing the template waveform with itself,
        measuring the parameter indicative of hemodynamic performance during a second state to establish a test waveform,
        performing a cross-characterization between the template waveform and the test waveform to identify a cross-characterization measure,
        comparing the cross-characterization measure with the autocharacterization measure to obtain a comparison result, and
        obtaining an indication of hemodynamic status based on the comparison result; and
    selecting, based on said indication of hemodynamic status, the appropriate anti-arrhythmia therapy to treat the arrhythmia.

2. The method of claim 1, wherein the obtaining an autocharacterization measure step comprises obtaining a maximum autocorrelation value for the template waveform.

3. The method of claim 2, wherein the performing step comprises performing a cross-correlation between the template waveform and the test waveform to identify a maximum cross-correlation value for the test waveform, wherein the maximum cross-correlation value comprises the cross-characterization measure.

4. The method of claim 3, wherein the comparing step comprises comparing the maximum cross-correlation value for the test waveform with the maximum autocorrelation value to obtain an indication of hemodynamic status.

5. The method of claim 4, wherein the comparing step comprises comparing a difference between the maximum autocorrelation value and the maximum cross-correlation value for the test waveform against a predetermined threshold.

6. The method of claim 5, wherein the difference comparing step comprises determining if the maximum cross-correlation value for the test waveform is less than the maximum autocorrelation value by a predetermined status low threshold, thereby determining if the hemodynamic status of the second state is low.

7. The method of claim 5, wherein the difference comparing step comprises determining if the maximum cross-correlation value for the test waveform is greater than the maximum autocorrelation value by a predetermined status high threshold, thereby determining if the hemodynamic status of the second state is high.

8. The method of claim 1, wherein the first measuring step comprises measuring a parameter indicative of hemodynamic performance during a normal sinus heart rhythm to establish a template waveform.

9. The method of claim 8, wherein the second measuring step comprises measuring the parameter indicative of hemodynamic performance during a tachycardia rhythm to establish a test waveform.

10. The method of claim 1, wherein the first measuring step comprises measuring a parameter indicative of hemodynamic performance during heart pacing with a baseline atrioventricular (AV) delay.

11. The method of claim 10, wherein the second measuring step comprises measuring the parameter indicative of hemodynamic performance during a test atrioventricular (AV) delay.

12. The method of claim 1, wherein the obtaining an autocharacterization measure step comprises cross-correlating the template waveform with itself to identify a maximum cross-correlation value for the template waveform, wherein the maximum cross-correlation value comprises the autocharacterization measure.

13. An implantable cardiac device comprising:
means for monitoring electrical activity of a patient's heart to detect an arrhythmia; and
a micro-controller configured to monitor hemodynamic performance of the heart, wherein the micro-controller is configured to:
obtain a parameter indicative of hemodynamic performance during a first state to establish a template waveform,
obtain an autocharacterization measure for the template waveform by cross-characterizing the template waveform with itself,
measure the parameter indicative of hemodynamic performance during a second state to establish a test waveform,
perform a cross-characterization between the template waveform and the test waveform to identify a cross-characterization measure,
compare the cross-characterization measure with the autocharacterization measure to obtain a comparison result, and
obtain an indication of hemodynamic status based on the comparison result; and
wherein the micro-controller is also configured to select, based on said indication of hemodynamic status, an appropriate anti-arrhythmia therapy to treat the arrhythmia.

14. The implantable cardiac device of claim 13, further comprising: means for delivering the appropriate anti-arrhythmia therapy to the heart.

15. The implantable cardiac device of claim 13, wherein the cross-characterization is a cross-correlation.

16. The implantable cardiac device of claim 15, wherein the cross-characterization measure is a maximum test value of the cross-correlation.

17. The implantable cardiac device of claim 16, wherein the autocharacterization measure is a maximum value of an autocorrelation of the template waveform.

18. The implantable cardiac device of claim 17, wherein to compare the cross-characterization measure with the autocharacterization measure, the micro-controller is configured to compare a difference between the maximum autocorrelation value and maximum test value against a predetermined threshold.

19. The implantable cardiac device of claim 18, wherein to compare a difference between the maximum autocorrelation value and maximum value against the predetermined threshold the micro-controller is configured to determine if the maximum test value is less than the maximum autocorrelation value by a predetermined status low threshold and determine if the hemodynamic status of the second state is low.

20. The implantable cardiac device of claim 18, wherein to compare a difference between the maximum autocorrelation value and maximum value against the predetermined threshold the micro-controller is configured to determine if the maximum test value is greater than the maximum autocorrelation value by a predetermined status high threshold and determine if the hemodynamic status of the second state is high.

21. The implantable cardiac device of claim 13, wherein to obtain an autocharacterization measure, the micro-controller is configured to cross-correlate the template waveform with itself and obtain a maximum cross-correlation value for the template waveform, wherein the maximum cross-correlation value comprises the autocharacterization measure.

* * * * *